US005700639A

United States Patent [19]

Trauth et al.

[11] Patent Number: 5,700,639
[45] Date of Patent: Dec. 23, 1997

[54] METHOD FOR THE DETECTION OF METABOLICALLY LABELLED DNA

[75] Inventors: Bernhard Trauth, Weilheim; Matthias Hinzpeter, München; Clemens Doppler, Seeshaupt; Eberhard Russmann, Penzberg, all of Germany

[73] Assignee: Boehringer Mannheim GmbH, Mannheim, Germany

[21] Appl. No.: 257,686

[22] Filed: Jun. 9, 1994

[30] Foreign Application Priority Data

Jun. 12, 1993 [DE] Germany ............. 43 19 506.7

[51] Int. Cl.⁶ ............. C12Q 1/68; G01N 33/53; G01N 33/537; G01N 33/543

[52] U.S. Cl. ............. 435/6; 435/7.1; 435/7.21; 435/7.5; 435/7.94; 435/18; 435/19; 435/173.7; 436/518; 436/528; 436/531; 436/538; 935/77

[58] Field of Search ............. 422/55, 57, 61; 435/6, 7.21, 7.5, 7.9, 18, 19, 28, 173.7, 195, 196, 975, 7.1, 7.94; 436/518, 528, 531, 544, 540, 538; 536/26.41, 26.6; 530/388.21, 389.8, 391.3; 935/77

[56] References Cited

U.S. PATENT DOCUMENTS

| | | | |
|---|---|---|---|
| 4,298,685 | 11/1981 | Parikh et al. | 435/7.93 |
| 4,496,654 | 1/1985 | Katz et al. | 435/7.94 |
| 4,623,627 | 11/1986 | Huang et al. | 435/6 |
| 4,656,127 | 4/1987 | Mundy | 435/6 |
| 4,812,394 | 3/1989 | Dolbeare et al. | 435/6 |
| 5,238,813 | 8/1993 | Lefkowith | 435/7.21 |
| 5,399,586 | 3/1995 | Davies et al. | 514/448 |

OTHER PUBLICATIONS

Monosov et al., 1992. Immunoelectron microscopy of deoxyribonucleic acid in procaryotic cells. Acta Histochem. Cytochem. 25: 137–141.

Hutchison et al., 1982. In situ hybridization at the electron microscope level: hybrid detection by autoradiography and colloidal gold. Journal of Cell Biology 95: 609–618.

Porstmann et al., 1985. Quantitation of 5–bromo–2–deoxyuridine incorporation into DNA: an enzyme immunoassay for the assessment of the lymphoid cell proliferative response. J. Immunological Methods 82: 169–179.

Martinon et al., 1987. In vitro proliferation of human lymphjocytes measured by an enzyme immunoassay using an anti–5–bromo–2–deoxyuridine monoclonal antibody. J. Clin. Lab. Immunol. 23: 153–159.

Death and the cell; Duvall et al. Immunology Today 7(4) 115–119 (1986).

*Primary Examiner*—Paula K. Hutzell
*Assistant Examiner*—James L. Grun
*Attorney, Agent, or Firm*—Felfe & Lynch

[57] ABSTRACT

The invention concerns a method for the non-radioactive detection of metabolically labelled DNA, in one aspect detecting labelled DNA indicative of cell lysis or apoptosis.

14 Claims, No Drawings

METHOD FOR THE DETECTION OF METABOLICALLY LABELLED DNA

The invention concerns a method for the non-radioactive detection of metabolically labelled DNA as well as a suitable reagent kit for carrying out this method.

The determination of the capability of cells to proliferate is of major importance for investigations in cell biology. In this process, the DNA of the cell population to be examined is metabolically labelled, i.e., the cells are supplied with labelled precursors of DNA biosynthesis which are incorporated by proliferating cells into DNA. In the standard method of metabolic labelling of genomic DNA, tritium-labelled thymidine is used as such a precursor. However, an increasing fragmentation of the labelled DNA is observed with increasing doses of the tritium-labelled thymidine and with an increasing labelling period (E. Solary et al., Experimental Cell Research 203 (1992), 495–498). The production of monoclonal antibodies against the thymidine analogue 5-bromo-2'-deoxyuridine enables the detection of non-radioactively labelled DNA that has been metabolically labelled by means of the incorporation of bromodeoxyuridine (H. Gratzner, Science 218 (1982), 474–475). Although at first a monoclonal antibody was also described which was claimed to recognize bromodeoxyuridine in native, i.e. non-denatured DNA (N. Gonchoroff et al., Cytometry 6 (1985), 506–512), in a later more exact investigation of the binding properties of monoclonal antibodies against bromodeoxyuridine, it was described that all previously known monoclonal antibodies against bromodeoxyuridine only bind to a bromodeoxyuridine in a single strand region (M. Miller et al., J. Immunol. 136 (1986), 1791–1795). Thus, when bromodeoxyuridine is used to metabolically label DNA, a denaturation of the DNA is necessary in order to detect the labelled DNA by binding of the antibody. In the described cellular test systems, the cells are fixed by treatment with HCl/ethanol and at the same time proteins bound to the DNA are detached and the DNA is denatured in this process. A disadvantage of these cellular test systems is, however, a high unspecific background as well as an undefined accessibility of the metabolically labelled DNA to the antibody since the entire cellular material is fixed. As a consequence it is not possible to carry out sufficiently reproducible quantitative determinations with such cellular test systems.

F. Martinon et al. (J. Clin. Lab. Immunol. 23 (1987), 153–159) describe a sandwich ELISA for the detection of DNA labelled with bromodeoxyuridine in which a first antibody against bromodeoxyuridine is used to immobilize the DNA and a further labelled antibody against bromodeoxyuridine is used to detect the bound DNA. Since in this case the metabolically labelled DNA to be detected must already be present as a single strand for binding to the solid phase, this method requires a time-consuming denaturation of the DNA to be examined in solution by treatment with acids or bases or a heat denaturation step before binding to the solid phase. Hence this method is too tedious and time-consuming for a routine determination of metabolically labelled DNA.

The object of the invention was therefore to provide a method for the detection of metabolically labelled DNA which is easy to carry out and enables reproducible quantitative determinations.

This object is achieved by a method for the non-radioactive detection of metabolically labelled DNA in a cell fraction which is characterized in that a) the cell fraction is incubated with an antibody which binds to DNA and this antibody is bound before or after incubation to a solid phase, b) the DNA is denatured, c) a labelled antibody against the metabolic label is added, d) the solid and liquid phase are separated and e) the label of the antibody from step c) is determined in one of the two phases as a measure of the metabolically labelled DNA.

The method according to the invention can be used to detect DNA which has been metabolically labelled in a conventional manner, for example by means of bromodeoxyuridine incorporation, in a simple manner and under reproducible conditions. The method according to the invention therefore simplifies the known methods for the determination of the capability of cells to proliferate in which the capability to proliferate is determined by metabolically labelling the DNA. The simple detection of a metabolically labelled DNA according to the invention is also of particular importance for the determination of the cytotoxicity of chemical compounds, antibodies or cytotoxic cells. In this case the influence of these compounds or cells on the capability of cells to proliferate is determined or cell damage is determined by detection of labelled DNA outside the cell nucleus of the cells to be examined.

The metabolic labelling for the test by the method according to the invention can be achieved by incorporating any desired nucleoside analogue of natural precursors of DNA biosynthesis provided this analogue is incorporated into the DNA in the same way as a natural precursor and an antibody against this analogue is known.

In order to carry out the method according to the invention, an antibody which binds to DNA is firstly bound directly or indirectly to a solid phase. This binding is carried out in a manner well-known to a person skilled in the art, for example by means of an adsorptive binding of the antibody to the solid phase or by binding of a biotinylated antibody that binds to DNA to a solid phase coated with streptavidin (production of a solid phase coated with streptavidin e.g. according to EP-A 0 269 092). Any antibody that binds directly to DNA or via a further binding partner can be used as the antibody that binds to DNA. Antibodies that bind directly to DNA are described for example in Andre-Schwartz et al., Clin. Immunol. Immunopathol. 31 (1984), 261. In addition it is also possible to use an antibody against a protein which is associated with DNA, such as a histone in particular, if it is intended to detect a metabolically labelled DNA that is associated with such a protein i.e. it contains this protein in a bound form. Each of these antibodies can be used as a complete immunoglobulin as well as a functional fragment of an immunoglobulin such as a Fab or F(ab')$_2$ fragment. The cell fraction used as the sample can either be the total DNA of a cell or a concentrated DNA fraction from the cell nucleus or the cytoplasm or even DNA fragments from the cell culture supernatant of lysed cells. In this case lysed cells are understood as those cells whose cytoplasmic membrane has been dissolved at least to the extent that cellular DNA or DNA fragments can pass from the cell into the cell culture supernatant. Such lysed cells are, for example, obtained by treatment with a detergent, preferably a non-ionic detergent or by incubation with cytotoxic T cells or natural killer cells. The DNA fragments obtained in this process can be used without pretreatment.

The metabolic labelling of the DNA or DNA fragments is preferably carried out by means of bromodeoxyuridine incorporation. A labelled antibody against bromodeoxyuridine is then used as the labelled antibody against the metabolic label. It has surprisingly turned out that it is possible to denature the bound DNA as required for antibody binding without the DNA which is only bound to the solid phase by means of an antibody becoming detached from the solid phase. The denaturation can in this case be carried out in a manner well-known to a person skilled in the art for a denaturation in solution or for cellular test systems e.g. by microwave treatment or by addition of a nuclease, preferably exonuclease III. For the denaturation by means of microwave treatment the reaction mixture is treated for 0.5 to 5 minutes with microwaves at a power of 500 to 1000 W. The denaturation by means of a nuclease is achieved by addition of 4 to 300 units/ml nuclease and incubation at 37° C. for 30 minutes in a Tris buffer (66 mmol/l Tris, 0.66 mmol/l $MgCl_2$ and 1 mmol/l 2-mercaptoethanol) at pH 7.5 to 8.5 and preferably pH 8.0.

After incubation of the denatured DNA with a labelled antibody against bromodeoxyuridine and separation of the solid and liquid phase, the metabolic label of the DNA can then be determined in a simple manner by means of the antibody label. This antibody can either be labelled directly with an enzyme, a chemiluminescent or fluorescent dye or for example be labelled by an appropriately labelled additional antibody.

Use of a cell culture supernatant as the sample solution for the method according to the invention enables the special detection of metabolically labelled DNA fragments of cells that have been lysed as a result of damage such as e.g. by cytotoxic T cells or natural killer cells (Berke, Immunol. Today 6 (1991) 21–27 and Berke, Immunol. Today 12 (1991), 396–399).

A preferred subject matter of the invention is therefore a variant of the method according to the invention in which the cell culture supernatant of lysed cells is added as the cell fraction.

In contrast to cells which have been lysed by cytotoxic T cells or natural killer cells, cells which have died by so-called apoptosis contain metabolically labelled DNA fragments only in the cytoplasm. Only after a longer incubation (more than 4 hours) do DNA fragments pass into the cell culture even in apoptotic cells as a result of secondary damage (which is a result of the long incubation period). Apoptosis is an active process of eukaryotic cells which leads to programmed cell death or is a result of an induced cell death such as is caused for example by chemical compounds such as camptothecin, dioxins or certain antibodies or by ionizing radiation (Duvall et al., Immunol. Today 7 (1986), 115–119). Thus by using a cytoplasmic cell fraction it is possible to also specially detect metabolically labelled DNA fragments of apoptotic cells in a further variant of the method according to the invention.

A particular preferred subject matter of the invention is therefore a variant of the method according to the invention in which a cytoplasmic cell fraction is incubated with the antibody that binds to DNA. In this process the cytoplasmic cell fraction is preferably obtained by treatment with a non-ionic detergent. Such detergents are known to a person skilled in the art. NP-40 (ethylphenyl polyethylene glycol), Tween 20 (polyoxyethylenesorbitan monolaurate) or Triton-X100 (octylphenol polyethylene glycol ether) is preferably used. They only lyse the cytoplasmic membrane but not the nuclear membrane of a eukaryotic cell. Since in apoptotic cells no metabolically labelled DNA passes into the cell culture supernatant, it is not necessary to separate the cell culture supernatant before isolating the cytoplasmic fraction. Therefore, it is possible to use a crude lysate as the cytoplasmic cell fraction which has been obtained by direct treatment of the cell culture with the said detergents.

The invention in addition concerns the use of the method according to the invention to determine the effect or activity of agents which cause apoptosis such as ionizing radiation or chemical compounds such as dioxins, certain antibodies or camptothecin.

Whereas the metabolically labelled DNA fragments that are detectable using the method according to the invention are already released after a short period into the cell culture supernatant in the case of cells which have been lysed with cytotoxic T cells, these fragments are only found in the cytoplasmic cell fraction during the usual incubation periods in cells which have died by means of apoptosis (see above). The method according to the invention is therefore suitable for differentiating between cells which have been lysed by cytotoxic T cells and apoptotic cells. For this, the DNA of the cell culture to be examined is metabolically labelled in a known manner preferably by means of bromodeoxyuridine incorporation. Subsequently, the method according to the invention is used to examine whether metabolically labelled DNA fragments can be detected in the cell culture supernatant or only in the cytoplasmic cell fraction in two parallel preparations. In order to detect metabolically labelled DNA fragments in the cytoplasmic fraction, the cell culture to be examined is treated with a non-ionic detergent as described above. Only in this preparation are metabolically labelled DNA fragments detectable in the cell culture supernatant also in the case of apoptotic cells. In contrast, in the second parallel preparation without detergent treatment, metabolically labelled DNA fragments are only detectable in the cell culture supernatant when cells are present which have been lysed by cytotoxic T cells.

The invention in addition concerns a reagent kit for the detection of metabolically labelled DNA fragments containing an antibody that binds to DNA as well as an antibody against the metabolic label. An antibody against bromodeoxyuridine is preferably used as the antibody against the metabolic label.

A preferred subject matter of the invention is therefore a reagent kit for the detection of metabolically labelled DNA fragments containing an antibody that binds to DNA as well as an anti-bromodeoxyuridine antibody.

A particularly preferred subject matter of the invention is a reagent kit according to the invention in which the antibody that binds to DNA is present in a biotinylated form for binding to a solid phase and which additionally contains a solid phase coated with streptavidin.

In addition, the invention finally concerns a reagent kit according to the invention which additionally contains a nuclease for denaturing the antibody-bound DNA. In this case exonuclease III is preferably used as the nuclease.

The invention is elucidated in more detail by the following examples.

EXAMPLE 1

Detection of metabolically labelled DNA fragments

The cells to be examined (e.g. HL60 cells, ATCC CCL 240) are firstly metabolically labelled by incubation with 0.01 mmol/l bromodeoxyuridine for 18 hours at 37° C. After removing the excess bromodeoxyuridine that is not incorporated into DNA by washing with culture medium, the cells (200 µl in each case, see Table 1 for cell number) are incubated for 4 hours at 37° C. with 2 µg/ml camptothecin (Sigma, Munich) in a microtitre plate. Afterwards 20 µl 10-fold concentrated lysis buffer (PBS/50 mmol/l EDTA/2 % Tween 20) is added to each preparation for the lysis, the microtitre plate is centrifuged and 100 µl supernatant is taken from each well for the test (PBS=137 mmol/l NaCl; 2.7 mmol/l KCl; 8 mmol/l $Na_2HPO_4$ and 1.5 mmol/l $KH_2PO_4$).

In order to detect the metabolically labelled DNA, a further microtitre plate is coated with an antibody against DNA (5 μg/ml, Boehringer Mannheim GmbH, Ident. No. 1525760) in 100 mmol/l NaCO$_3$ buffer pH 9.6. Subsequently the metabolically labelled DNA is bound to the wall antibody by addition of 100 μl supernatant (see above) per well and incubation for 90 minutes at room temperature. After washing with PBS, the remaining liquid is removed from the wells of the microtitre plate by for example knocking. Afterwards the bound double-stranded DNA is denatured or partially degraded by microwave treatment (5 min. 650 watts, AEG Micromat 275Z) or alternatively by addition of 100 μl (corresponding to 1 unit per well of the microtitre plate) exonuclease III (Boehringer Mannheim GmbH, Catalogue No. 779717). The preparation in which the DNA has been denatured by microwave treatment is subsequently cooled for 10 minutes at 8° C. in a refrigerator. The preparation treated with exonuclease III is subsequently washed three times with PBS. Afterwards 100 μl per well of a peroxidase-labelled antibody against bromodeoxyuridine (Boehringer Mannheim GmbH, Catalogue No. Ident. No. 1 449 338, 250 mU/ml) is added to both of the preparations and bound antibody and hence labelled DNA fragments are determined by means of the peroxidase reaction using ABTS® as a substrate (100 μl per well, Boehringer Mannheim GmbH, Catalogue No. 1204521) and measuring the absorbance at 405 nm. The following Table 1 shows the good correlation between the measured signal obtained and the amount of metabolically labelled DNA in the denaturation by means of microwave treatment and in the denaturation by nuclease treatment.

TABLE 1

Detection of metabolically labelled DNA fragments

| Number of prelabelled cells | A (405 nm) in the denaturation with 1 unit nuclease per well | A (405 nm) in the denaturation by means of microwave |
| --- | --- | --- |
| 6 × 10$^3$ | 0.870 | 0.752 |
| 3 × 10$^3$ | 0.572 | 0.420 |
| 1.5 × 10$^3$ | 0.348 | 0.257 |
| 7.5 × 10$^2$ | 0.195 | 0.148 |
| 3.75 × 10$^2$ | 0.099 | 0.077 |

EXAMPLE 2

Detection of metabolically labelled DNA fragments in the culture supernatant of cells which have been lysed by cytotoxic T cells Cells of the murine P815 cell line (ATCC TIB 64) are metabolically labelled as described in example 1 with bromodeoxyuridine. After washing out excess bromodeoxyuridine, 2×10$^4$ cells (100 μl) are incubated in each case in a microtitre plate at 37° C. for 4 hours with different amounts of allogen-stimulated cytotoxic T cells (see Table 2 for the effector to target cell ratios) (the production of cytotoxic T cells was carried out according to Current Protocols in Immunology, eds. J. Coligan, A. Kruisbeek, D. Margulies, E. Shevach and W. Strober, John Wiley and Sons, New York (1992), chapter 3.11). Afterwards the microtitre plate is centrifuged and in each case 100 μl supernatant of each preparation is used for the determination which is carried out as described in example 1 via denaturation by microwave treatment.

The following Table shows that the amount of metabolically labelled DNA which can be determined in the cell culture supernatant correlates with the amount of added effector cells and thus with the degree of cytotoxic activity. In contrast no metabolically labelled DNA is detectable in the cell culture supernatant of P815 target cells incubated without effector cells and in the cell culture supernatant of the cytotoxic effector cells.

TABLE 2

Detection of metabolically labelled DNA fragments in the cell culture supernatant of cells which have been lysed by cytotoxic T cells.

| Ratio of cytotoxic T cells to target cells | A (405 nm) cytotoxic T cells plus target cells[1] | A (405 nm) cytotoxic T cells without target cells[2] |
| --- | --- | --- |
| 12:1 | 0.977 | 0.010 |
| 6:1 | 1.092 | 0.007 |
| 3:1 | 0.894 | 0.0 |
| 1.5:1 | 0.752 | 0.009 |
| 0.75:1 | 0.620 | 0.001 |
| 0.4:1 | 0.464 | 0.0 |

1) Likewise no significant amount of metabolically labelled DNA could be detected (A (405 nm) 0.073) in the cell culture supernatant of an identical amount of P815 target cells which had been incubated in the absence of cytotoxic T cells.
2) The cell culture supernatant of a corresponding amount of cytotoxic T cells which had been incubated without prelabelled target cells was used as a control.

EXAMPLE 3

Detection of metabolically labelled DNA fragments in the cytoplasm of apoptotic cells HL60 cells (ATCC CCL 240) were firstly metabolically labelled with bromodeoxyuridine as stated in example 1. After washing out excess bromodeoxyuridine, the cells are incubated in a microtitre plate at 37° C. for 3 or 4 hours with various concentrations of camptothecin (5000 to 0 ng/ml). Subsequently the microtitre plate is centrifuged, an aliquot of the cell culture supernatant (100 μl/well) is taken for the detection of metabolically labelled DNA in the cell culture supernatant according to example 2 and the cells remaining in the microtitre plate are lysed by addition of 100 μl/well 2-fold concentrated lysis buffer (PBS/10 mmol/l EDTA/ 0.4% Tween 20). The detection of the metabolically labelled DNA in the lysate obtained in this way is then carried out as described in example 1.

Table 3 shows that in the case of the preparation incubated for 3 hours, metabolically labelled DNA in the apoptotic cells is only detectable in the cytoplasmic fraction (i.e. only after treatment with a detergent in the supernatant) but not in the cell culture supernatant.

Table 4 shows that in the case of the preparation incubated for 4 hours, the amount of these cytoplasmic, metabolically labelled DNA fragments correlates with the amount of camptothecin i.e. with the activity which triggers an apoptosis.

TABLE 3

Detection of metabolically labelled DNA fragments in apoptotic cells

| | A (405 nm) | A (405 nm) apoptosis |
| --- | --- | --- |

| Fraction | control (0 ng/ml camptothecin) | (200 ng/ml camptothecin) |
|---|---|---|
| Cell culture supernatant (according to example 2) | 0.011 | 0.020 |
| cytoplasm (lysate after detergent treatment) | 0.068 | 0.770 |

TABLE 4

Detection of metabolically labelled DNA fragments in the cytoplasm of apoptotic cells

| Camptothecin (ng/ml) | A (405 nm) |
|---|---|
| 5000 | 1.677 |
| 1000 | 1.457 |
| 200 | 1.006 |
| 40 | 0.625 |
| 8 | 0.342 |
| 1.6 | 0.295 |
| 0 | 0.265 |

We claim:

1. Method for measuring DNA synthesis in a cell, comprising:

(a) metabolically incorporating a nucleotide analogue into a double stranded DNA of said cell;

(b) incubating a cell fraction of said cell containing said double stranded DNA having incorporated therein said nucleotide analogue in the presence of a first antibody specific to DNA to obtain a double stranded DNA-first antibody complex, wherein said first antibody is bound to a solid phase prior to or after said incubating;

(c) denaturing or partially degrading said double stranded DNA bound to said first antibody without separating said first antibody from said solid phase, thereby providing denatured DNA or partially degraded DNA bound to said first antibody;

(d) contacting said bound denatured or partially degraded DNA with a labeled second antibody specific to said nucleotide analogue under conditions favoring binding of said labelled second antibody to said nucleotide analogue present in said bound denatured or partially degraded DNA, (e) separating the solid phase from reagents in liquid phase; and (f) measuring a level of labelled second antibody on said solid phase or in said liquid phase as a measure of nucleotide analogue incorporation into the DNA of said cell thereby measuring the DNA synthesis of the cell.

2. The method of claim 1, wherein said first antibody is bound to said solid phase prior to said incubating.

3. The method of claim 1, wherein said first antibody is bound to said solid phase after said incubating.

4. The method of claim 1, wherein said nucleotide is 5-bromo-2'-deoxyuridine and said second antibody is specific to bromodeoxyuridine.

5. The method of claim 1, wherein said denaturing or partial degrading comprises treatment with microwaves or an exonuclease.

6. The method of claim 1, wherein said first antibody is biotinylated and said solid phase is coated with streptavidin.

7. The method of claim 1, wherein said cell fraction is a cell culture supernatant of a cell that has been lysed.

8. The method of claim 1, wherein said cell fraction is a cytoplasmic fraction of said cell.

9. Method for distinguishing between lytic or apoptotic mechanism of a cytotoxic agent or cell action on a sample of cells comprising:

(a) incorporating a nucleotide analogue into the double stranded DNA of a sample of cells in culture medium;

(b) contacting said sample having incorporated therein said nucleotide analogue with a cytotoxic agent or cell population for a period of 4 hours or less;

(c) separating said sample of cells into a first group and a second group;

(d) contacting the first group with an agent that lyses cells by lysing the cell membranes thereof but not the nuclear membrane of said cells, to obtain a cytoplasmic cell fraction and a nuclear fraction;

(e) incubating said cytoplasmic cell fraction obtained in step (d) in the presence of a first antibody specific to DNA to obtain a double stranded DNA-first antibody complex, wherein said first antibody is bound to a solid phase prior to or after said incubating;

(f) incubating a cell culture supernatant cell fraction from the second group in the presence of a first antibody specific to DNA to obtain a double stranded DNA first antibody complex, wherein said first antibody is bound to a solid phase prior to or after said incubating;

(g) for each of the cell fractions from said first and said second groups according to steps (e) and (f):

(i) denaturing or partially degrading said double stranded DNA bound to said first antibody without separating said first antibody from said solid phase, thereby providing denatured or partially degraded DNA bound to said first antibody, (ii) contacting said bound denatured or partially degraded DNA with a labeled second antibody specific to said nucleotide analogue under conditions favoring binding to said bound denatured or partially degraded DNA;

(iii) separating the solid phase from reagents in liquid phase;

(iv) measuring a level of labelled second antibody on said solid phase or in said liquid phase as a measure of a level of DNA in said cell fraction; and (h) comparing the levels of DNA obtained in step (g) (iv) for said cell fractions from said first and second groups, wherein the presence of DNA in both the cytoplasmic cell fraction from the first group and the cell culture supernatant cell fraction from the second group is indicative of a lytic mechanism of action of said cytotoxic agent or cell population and, wherein the presence of DNA only in said cytoplasmic cell fraction from the first group is indicative of an apoptotic mechanism of action of said cytotoxic agent or cell population.

10. The method of claim 9, wherein said first antibody is bound to said solid phase prior to said incubating.

11. The method of claim 9, wherein said first antibody is bound to said solid phase after said incubating.

12. The method of claim 9, wherein said nucleotide is 5-bromo-2'-deoxyuridine and said second antibody is specific to bromodeoxyuridine.

13. The method of claim 9, wherein said denaturing or partially degrading comprises treatment with microwaves or an exonuclease.

14. The method of claim 9, wherein said first antibody biotinylated and said solid phase is coated with streptavidin.

* * * * *

UNITED STATES PATENT AND TRADEMARK OFFICE
CERTIFICATE OF CORRECTION

PATENT NO. : 5,700,639
DATED : December 23, 1997
INVENTOR(S) : Bernhard TRAUTH et al.

It is certified that error appears in the above-identified patent and that said Letters Patent is hereby corrected as shown below:

In Claim 9(f), column 8, line 21, between "DNA" and "first" insert -- -- --.

In Claim 14, column 8, line 64, after "antibody" insert -- is --.

Signed and Sealed this

Second Day of May, 2000

*Attest:*

Q. TODD DICKINSON

*Attesting Officer*    *Director of Patents and Trademarks*